US00PP25423P2

(12) United States Plant Patent
Hartman

(10) Patent No.: US PP25,423 P2
(45) Date of Patent: Apr. 7, 2015

(54) ***CALADIUM* PLANT NAMED 'DEBUTANTE'**

(50) Latin Name: *Caladium×hortulanum*
Varietal Denomination: Debutante

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 135 days.

(21) Appl. No.: 13/986,548

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Debutante', characterized by its compact, upright and uniformly mounding plant habit; vigorous growth habit and rapid growth rate; lance-type leaves with white-colored background variably tinged with pink and with distinct dark green-colored venation and red purple-colored leaf notch; and good landscape performance.

4 Drawing Sheets

Botanical designation: *Caladium×hortulanum.*
Cultivar denomination: 'DEBUTANTE'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Debutante'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'White Wonder', disclosed in U.S. Plant Pat. No. 21,044, as the female, or seed, parent with *Caladium×hortulanum* 'Florida Sweetheart', disclosed in U.S. Plant Pat. No. 8,526, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Lake Placid, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Debutante'. These characteristics in combination distinguish 'Debutante' as a new and distinct *Caladium* plant:

1. Compact, upright and uniformly mounding plant habit.
2. Vigorous growth habit and rapid growth rate.
3. Lance-type leaves with white-colored background variably tinged with pink and with distinct dark green-colored venation and red purple-colored leaf notch.
4. Good landscape performance.

Plants of the new *Caladium* differ primarily from plants of the female parent, 'White Wonder', in leaf color as plants of 'White Wonder' have leaves with white-colored background blushed with pink and distinct dark green-colored margins. In addition, plants of the new *Caladium* grow faster and produce finished plants one to two weeks earlier than plants of 'White Wonder'.

Plants of the new *Caladium* differ primarily from plants of the male parent, 'Florida Sweetheart', in leaf color as plants of 'Florida Sweetheart' have leaves with rose red-colored centers with distinct dark green-colored margins.

Plants of the new *Caladium* can be compared to plants of *Caladium×hortulanum* 'Candidum', not patented. In side-by-side comparisons, plants of the new *Caladium* differed primarily from plants of 'Candidum' in the following characteristics:

1. Plants of the new *Caladium* were more compact and mounding than plants of 'Candidum'.
2. Leaves of plants of the new *Caladium* were lance-type whereas leaves of 'Candidum' were fancy-type.
3. Plants of the new *Caladium* and 'Candidum' differed in leaf coloration as plants of 'Candidum' had white-colored leaves with dark green-colored venation.

Plants of the new *Caladium* can be compared to plants of *Caladium×hortulanum* 'White Delight', disclosed in U.S. Plant Pat. No. 21,216. In side-by-side comparisons, plants of the new *Caladium* differed primarily from plants of 'White Delight' in the following characteristics:

1. Plants of the new *Caladium* were more compact and mounding than plants of 'White Delight'.
2. Plants of the new *Caladium* grew faster and produced finished plants about one to two weeks earlier than plants of 'White Delight'.
3. Plants of the new *Caladium* had broader leaves than plants of 'White Delight'.
4. Plants of the new *Caladium* and 'White Delight' differed in leaf coloration as leaves of plants of 'White Delight' were white to grey-green in color with white-colored main veins and green-colored or speckled margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Debutante' in a 15-cm container and grown in a shadehouse.

The photograph at the top of the second sheet is a comparison view of typical plants of 'Debutante' grown in 15-cm containers; the plant on the left has not had its tuber de-eyed and the plant on the right has had its tuber de-eyed prior to planting.

The photograph at the bottom of the second sheet is a close-up view of a typical freshly-harvested tuber and roots of 'Debutante'.

The photograph on the third sheet is a close-up view of typical plants of 'Debutante' grown in an open field.

The photograph at the top of the fourth sheet is a comparison view of typical potted plants of 'Candidum' (left), 'Debutante' (center) and 'White Delight' (right).

The photograph at the bottom of the fourth sheet is a comparison view of typical potted plants of the female parent, 'White Wonder' (left), 'Debutante' (center) and the male parent, 'Florida Sweetheart' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (Outdoor nursery). Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Debutante'.

Parentage:

*Female, or seed, parent.*—*Caladium×hortulanum* 'White Wonder', disclosed in U.S. Plant Pat. No. 21,044.

*Male, or pollen, parent.*—*Caladium×hortulanum* 'Florida Sweetheart', disclosed in U.S. Plant Pat. No. 8,526.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to elliptic in shape. Height: About 3.2 cm to 4 cm. Diameter: About 3.8 cm. Segment height: About 1.5 cm to 1.8 cm. Segment diameter: About 1.5 cm to 2 cm. Texture: Thick, starchy; somewhat brittle. Color: Epidermis, freshly-harvested: Close to 199A to 199B and 200B. Epidermis, dried: Close to 200A to 200B. Cortical tissue: Close to 4C to 4D. Axillary buds: Close to 36A to 36B. Root description: Thick, fleshy contractile roots; color, close to 155D. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounding plant habit; vigorous and dense growth habit; rapid growth rate, potted plants in finished or saleable form in about six to seven weeks after planting tubers; leaf petioles and leaves arise from one or more growing points on tubers; petioles mostly upright and arching outwardly with development.

*Plant height, from soil level to top of foliar plane, shadehouse-grown potted plants.*—About 23 cm to 31 cm.

*Plant diameter or spread, shadehouse-grown potted plants.*—About 30 cm to 37 cm.

*Number of clumps per plant, shadehouse-grown potted plants.*—About three to four from de-eyed tubers.

*Cataphylls, shadehouse-grown potted plants.*—Length: About 3 cm to 4.5 cm. Width: About 1.2 cm. Shape: Wedge-shaped. Apex: Acute to acuminate. Base: Sheathing the stem. Color, outer surface: Close to 195C tessellated with close to 147B and tinged with close to N199B; with development, color becoming closer to 200C stained with close to 187A to 187B. Color, inner surface: Close to N155C; outer surface colors and patterns visible.

Foliage description:

*Arrangement and type.*—Alternate; simple; lance-type.

*Length, shadehouse-grown potted plants.*—About 16.5 cm to 20 cm.

*Width, shadehouse-grown potted plants, flattened.*—About 14 cm to 15.5 cm.

*Shape.*—Ovate to cordate.

*Apex.*—Acute to acuminate.

*Base.*—Sagittate, peltate; basal lobes, rounded.

*Margin.*—Entire; mostly flat, somewhat wavy with broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing leaves, upper surface: Background color: Close to N155D and 155C variably tinged with close to 51C, 51D and 184C. Basal notch: Close to 187A and 187B. Midvein and primary venation: Close to 147A. Secondary venation: Close to 147A to 147B. Developing leaves, lower surface: Background color: Close to 155B, 155C, 147B to 147C and 191A variably tinged with close to 50D and 51D. Basal notch: Close to 187A and 187B. Midvein: Close to 147D tinged with close to 146D. Primary venation: Close to 147B. Secondary venation: Close to 147B and 191A. Fully expanded leaves, upper surface: Background color: Close to 155C to whiter than 155C variably and faintly tinged with close to 50D and 148D. Basal notch: Close to 187B and 187C. Midvein and primary venation: Close to 147A. Secondary venation: Close to 147A and 146B. Fully expanded leaves, lower surface: Background color: Close to 155C. Basal notch: Close to 187B and 187C. Midvein: Close to 147D tinged with close to 146D. Primary venation: Close to 147B to 147C. Secondary venation: Close to 147C and 146D.

*Petiole*.—Aspect: Initially upright and straight; with development, leaning outwardly; flexible. Length, shadehouse-grown potted plants: About 17 cm to 24 cm. Diameter, distal, shadehouse-grown potted plants: About 4 mm. Diameter, proximal, shadehouse-grown potted plants: About 6 mm to 10 mm. Color, shadehouse-grown potted plants: Just below leaf and petiole junction, close to 193A and 194A often tinged or striped with close to N199B; proximally, close to 147B to 147C, N170D and 147D streaked and stippled with close to N199B tinged with close to 147C; variably and boldly striped with close to 200A to 200B. Wing length, shadehouse-grown potted plants: About 4 cm. Wing diameter, shadehouse-grown potted plants: About 8 mm. Wing color, shadehouse-grown potted plants, outer surface: Close to 195C tessellated with close to 147B tinged with close to N199B, or close to 196C tessellated, flushed and mottled with close to N199B. Wing color, shadehouse-grown potted plants, inner surface: Close to N155C; outer surface colors and patterns visible.

Inflorescence description: Inflorescence development has not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Debutante' as illustrated and described.

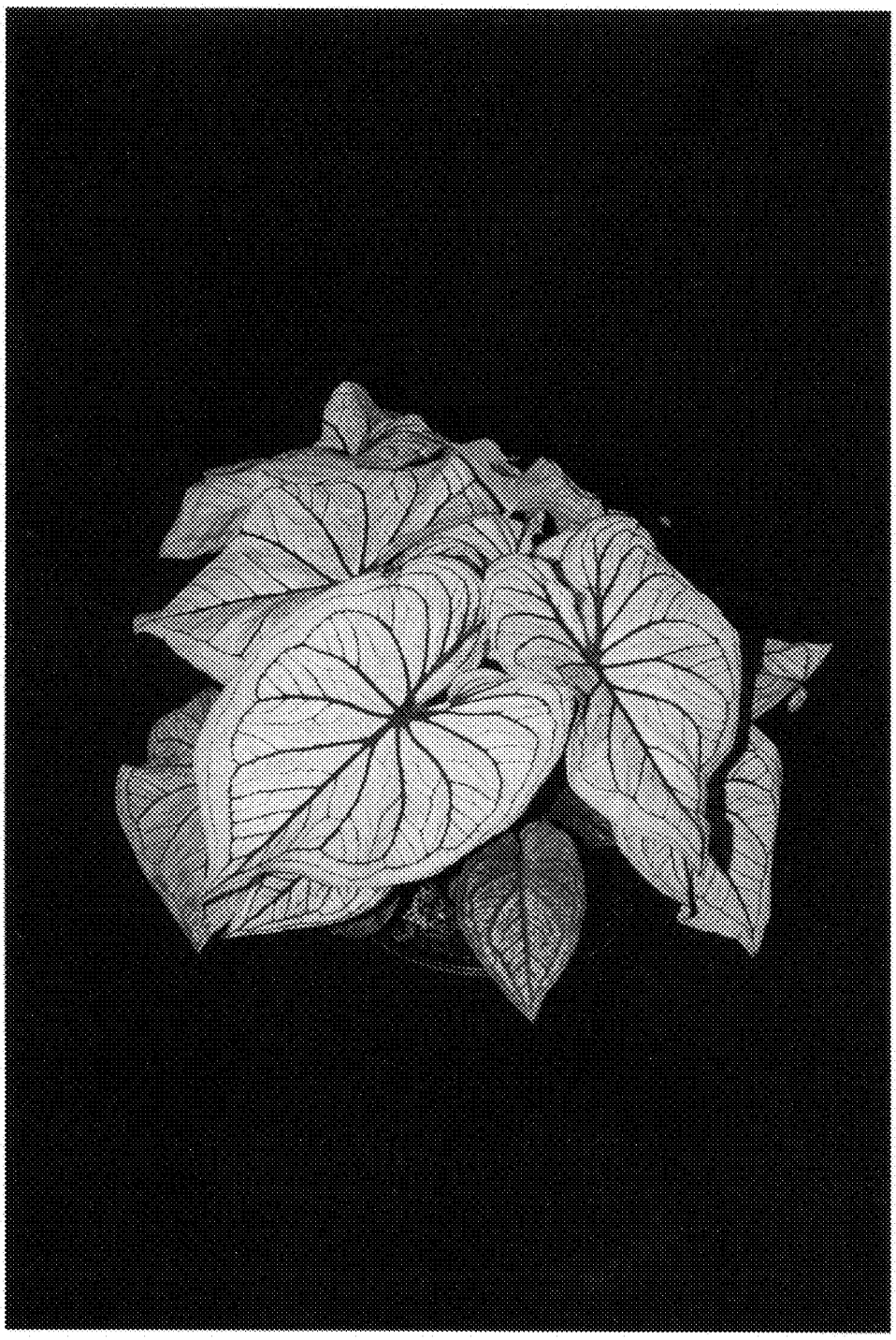

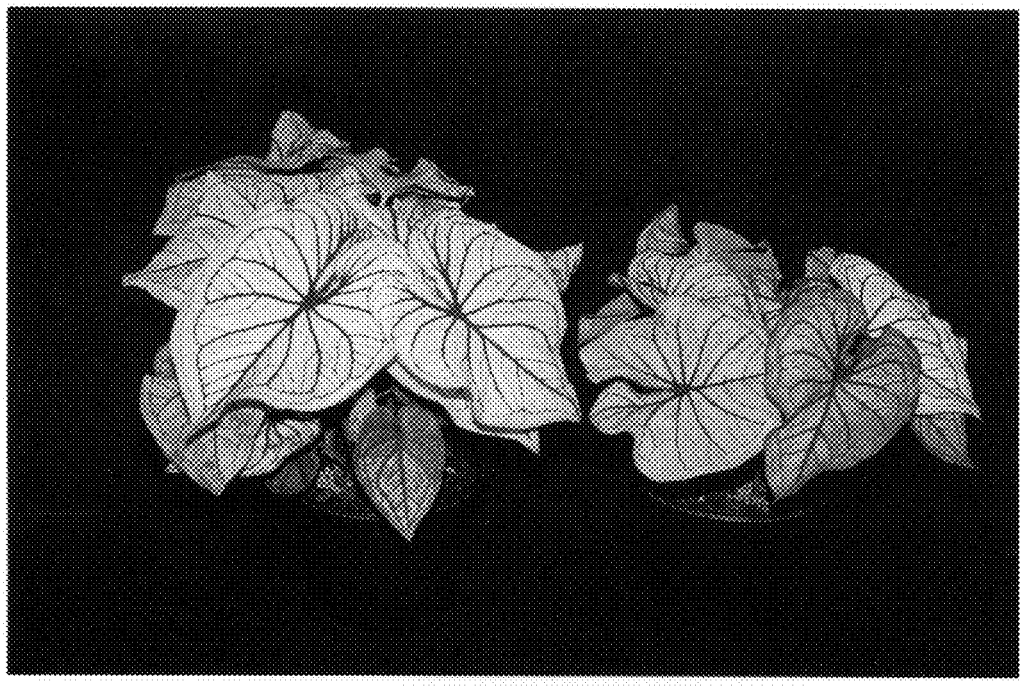
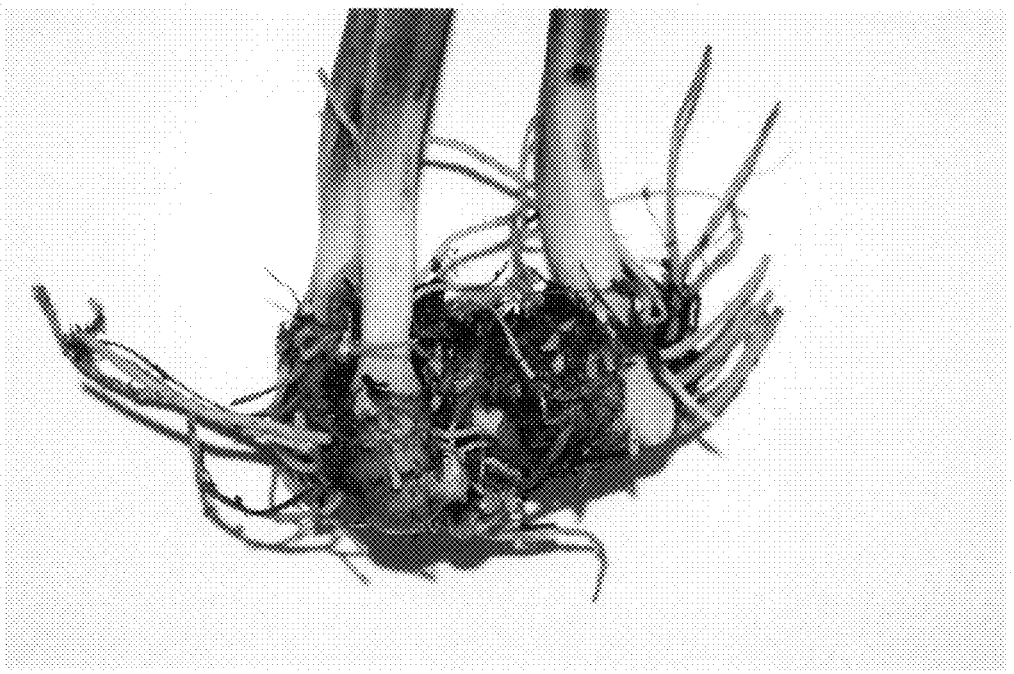

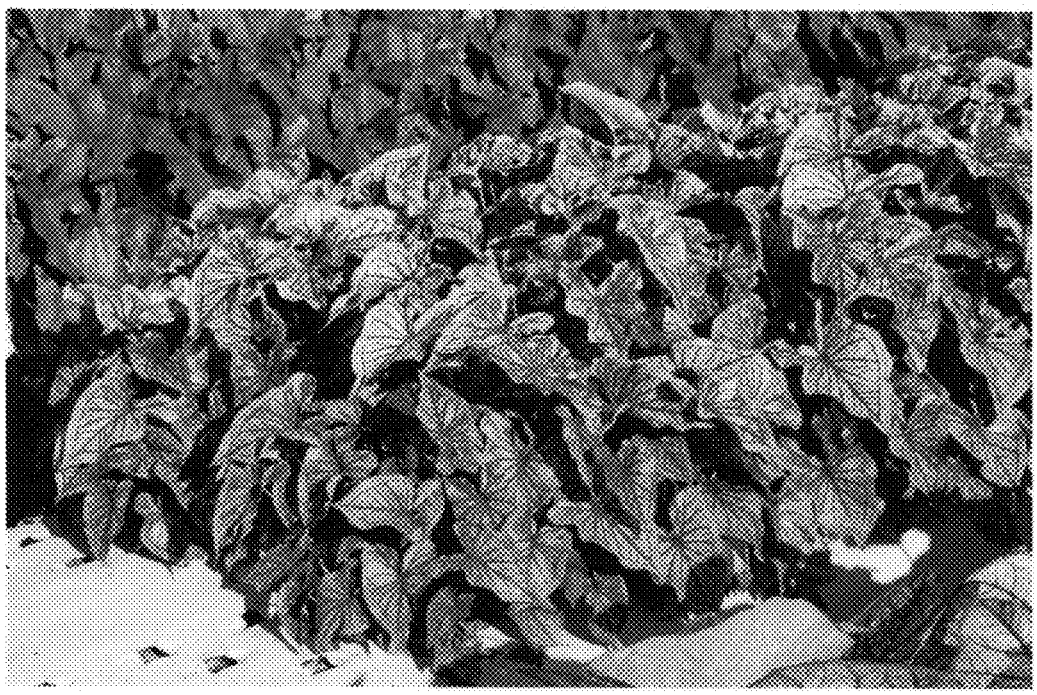

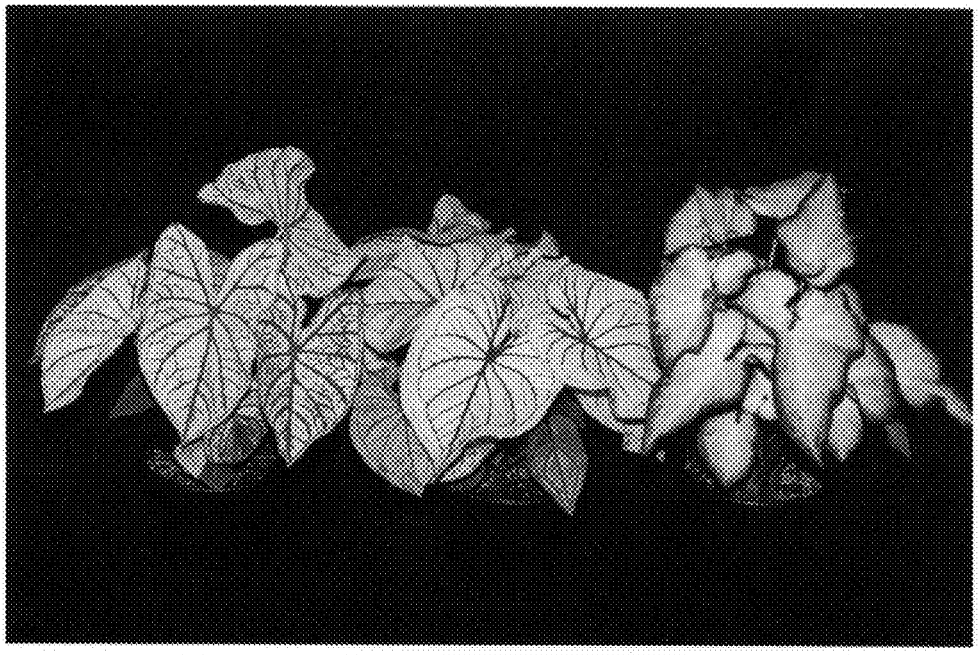
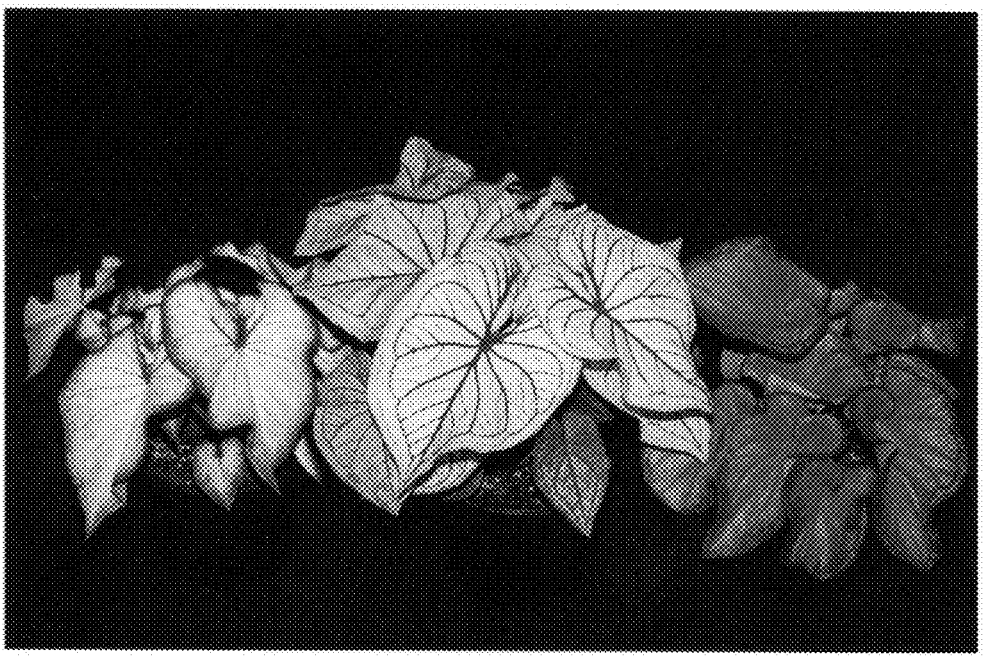

* * * * *